United States Patent [19]

Rosenberg et al.

[11] Patent Number: 4,596,575
[45] Date of Patent: Jun. 24, 1986

[54] LIQUID DELIVERY SYSTEM PARTICULARLY USEFUL AS AN IMPLANTABLE MICROPUMP FOR DELIVERING INSULIN OR OTHER DRUGS

[75] Inventors: Meir Rosenberg, Tel Aviv; Itzhak Teneboim, Petach Tiqwa; Jacob Lazarovitz, Jaffa, all of Israel

[73] Assignee: Omikron Scientific Ltd., Rehovot, Israel

[21] Appl. No.: 613,247

[22] Filed: May 23, 1984

[30] Foreign Application Priority Data

Aug. 4, 1983 [IL] Israel .................................. 69431

[51] Int. Cl.⁴ .............................................. A61M 5/14
[52] U.S. Cl. ............................ 604/891; 128/DIG. 12
[58] Field of Search ............... 604/890, 891, 151, 153, 604/212; 417/472–473; 128/DIG. 12

[56] References Cited

U.S. PATENT DOCUMENTS

| 3,894,538 | 7/1975 | Richter | 604/891 |
| 4,140,122 | 2/1979 | Kuhl et al. | 604/891 |
| 4,360,019 | 11/1982 | Portner et al. | 604/151 X |
| 4,411,651 | 10/1983 | Suhvlmin | 604/891 X |
| 4,443,218 | 4/1984 | De Cant et al. | 128/DIG. 12 |
| 4,511,355 | 4/1985 | Franetzki et al. | 604/153 X |

OTHER PUBLICATIONS

Spencer et al., "Elect. Controlled Piezo. Insulin Pump . . . ", IEEE Transactions on Sonics & Ultrasonic, vol. SU-25, No. 3, 5/78, pp. 153-156.
Suhvbert et al., "Implantable Artificial Pancreas", Med. & Biol. Eng. & Comput. 7/1980, pp. 527-537.

Primary Examiner—Edward M. Coven
Attorney, Agent, or Firm—Benjamin J. Barish

[57] ABSTRACT

A liquid delivery system, particularly useful as an implantable micro-pump for delivering insulin or other drugs, comprises a collapsible reservoir for the feed liquid to be delivered, which reservoir is enclosed by a rigid housing, a container for a drive liquid, and a pump selectively pumping the drive liquid either from the drive liquid container into the rigid housing between its inner face and the collapsible reservoir for pumping the feed liquid therefrom, or out of the rigid housing into the drive liquid container for refilling the collapsible reservoir with feed liquid.

25 Claims, 2 Drawing Figures

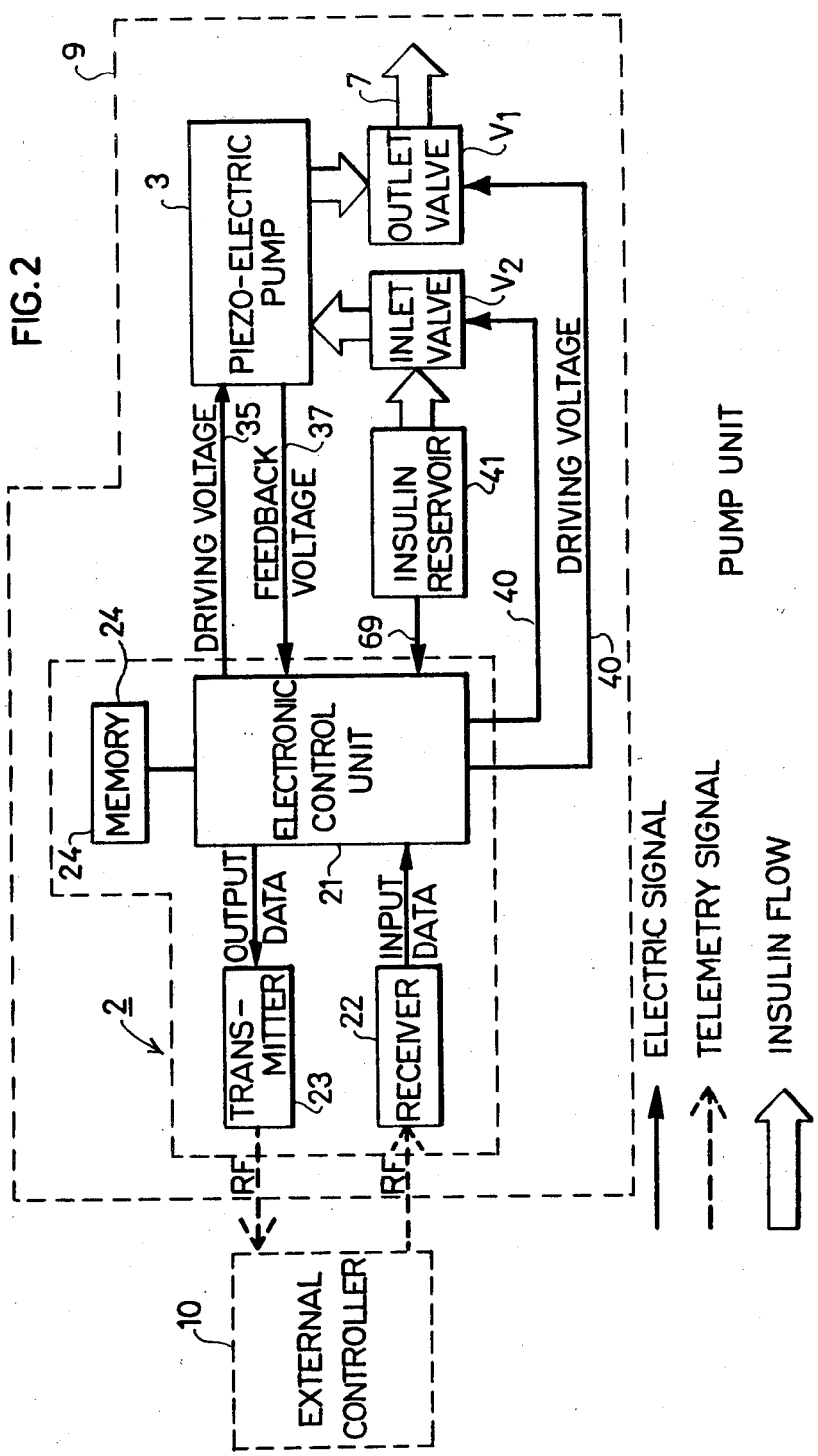

LIQUID DELIVERY SYSTEM PARTICULARLY USEFUL AS AN IMPLANTABLE MICROPUMP FOR DELIVERING INSULIN OR OTHER DRUGS

BACKGROUND OF THE INVENTION

The present invention relates to liquid delivery systems. The invention is particularly useful as an implantable micro-pump for delivering insulin or other drugs, and is therefore described with respect to such application, but it will be appreciated that the invention, or various aspects of it, could advantageously be used in other applications as well.

A number of liquid delivery systems or micro-pumps have been devised and are described in the literature, but the known ones suffer from a number of drawbacks, particularly when used as an implantable unit for delivering insulin or other drugs to the human body. Thus, in some of the known systems, there is a rapid deterioration of the insulin or other drug being delivered because of a number of factors including incompatability with the material of the container or other elements of the system with which the feed liquid comes into contact, and/or shear forces applied to the liquid arising from opening and closing of valves, turbulent flow, and the like. Another difficulty is the danger of overdosage or overfilling of the feed liquid or other drug reservoir during refilling, which can result in serious bodily harm or even death. Further difficulties are the requirements for high accuracy in the dosage, and the prevention of air bubbles, which are very hard to fulfill in the known pumping systems, particularly the non-self-priming pumps.

SUMMARY OF THE INVENTION

An object of the present invention is to provide a liquid delivery system having advantages in up to all of the foregoing respects.

According to one broad aspect of the present invention, there is provided a liquid delivery system comprising: a collapsible reservoir for a feed liquid to be delivered; a rigid housing enclosing the collapsible reservoir; a container for a drive liquid; a refill container and pumping means for selectively pumping the drive liquid either from the drive liquid container into the rigid housing between its inner face and the collapsible reservoir for pumping the feed liquid therefrom, or out of the rigid housing into the drive liquid container for refilling the collapsible reservoir with feed liquid from the refill container.

According to one important feature of the invention, the drive liquid container is also a collapsible container and is also disposed within a rigid housing; the interior of the latter rigid housing being maintained under sub-ambient pressure so that in the event of malfunction of the pumping means, the sub-ambient pressure tends to draw the drive liquid into its collapsible container, and thereby provides fail-safe protection against the pumping out of the feed liquid from its reservoir.

According to further features of the invention, the refill container is selectively connectible to the inlet of the feed liquid reservoir for refilling same. The system further includes means effective upon connection of the refill container to the inlet of the feed liquid reservoir for automatically actuating the pumping means to pump the drive liquid into its container, and thereby to cause the supply of feed liquid to be drawn into its reservoir from the refill container. In the described system, the pumping means are electrically energized and are controlled by a control system including an electrical switch actuated upon the connection of the refill container to the inlet of the feed liquid reservoir Further, the control system includes a memory which continuously stores a value representing the quantity of feed liquid delivered by the pumping means, the pumping means being actuated by the electrical switch to cause a quantity of feed liquid to be drawn into its collapsible reservoir from the refill container corresponding to the stored quantity of feed liquid previously delivered by the pumping means, and thereupon to automatically terminate the operation of the pumping means.

BRIEF DESCRIPTION OF THE DRAWINGS

Additional features and advantages of the invention will be apparent from the description below.

The invention is herein-described, by way of example only, with reference to the accompanying drawings, wherein:

FIG. 2 is a block diagram illustrating the control of the liquid delivery system of FIG. 1.

DESCRIPTION OF A PREFERRED EMBODIMENT

Figure 1:
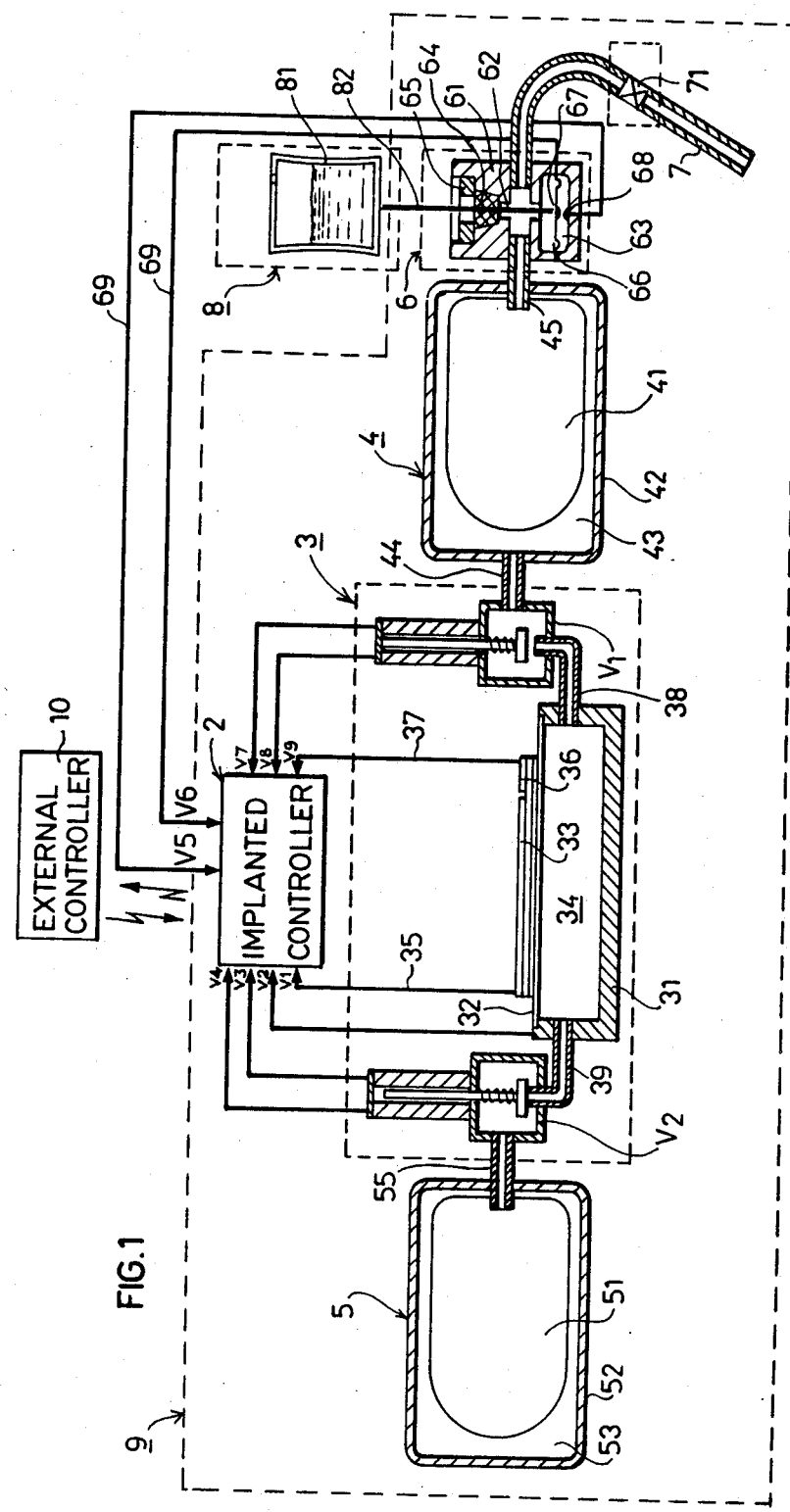
FIG. 1 illustrates one form of liquid delivery system constructed in accordance with the invention.

The liquid delivery system illustrated in the drawings is an implantable, remotely-programmable insulin (or other drug) infusion system. Briefly, it includes a controller 2 which controls a pump 3 such as to deliver the insulin from an insulin-feed unit 4. Pump 3 does not act directly on the insulin within unit 4, but rather indirectly by means of a drive liquid supplied from a drive liquid unit 5. The insulin (or other feed liquid) from unit 4 is pumped under the control of controller 2 out of unit 4 into the body via a fitting 6 and a feed tube 7. The illustrated system further includes a refill unit 8 adapted to be connectable to the insulin unit 4 for refilling it.

All the above-mentioned units illustrated in FIG. 1, except the refill unit 8, may be incorporated in an overall self-contained assembly, as shown by the broken lines 9, for implanting in a living body. Besides the external refill unit 8, the system further includes an external controller 10, which may be a hand held unit, adapted to communicate with the implanted controller 2 for inputting and outputting information with respect thereto.

The implanted controller 2 and the external controller 10, which may be of known construction such as described in Med. Progr. Technol. 9,17-25(1982), control the operation of the pump 3 according to a program inputted via the external controller 10. Thus, as shown in FIG. 2, the implanted controller 2 includes an electronic control unit 21, a receiver 22 for receiving information from the external controller 10, via an RF carrier wave, and a transmitter 23 for transmitting, also via an RF carrier wave, information to the external controller 10. Since such programmable controllers are known, details of the construction and operation of controllers 2 and 10 are not set forth herein except to the extent necessary to enable understanding the present invention.

According to one feature of the present invention, the implanted controller 2 includes a memory, indicated as 24 in FIG. 2, which continuously stores a value representing the quantity of insulin delivered by the pumping unit 3. This stored quantity is used for, among other purposes, controlling the refilling operation in which unit 4 is automatically refilled from the refill unit 8 with the quantity of insulin previously delivered since the last refill operation, thereby minimizing the possibility of over-filling or under-filling unit 4.

Pumping unit 3 is preferably a piezoelectrically driven micro-pump generally similar to that described in Bessman et al., U.S. Pat. No. 4,344,743 but including a number of differences. This pump 3 includes a housing 31 in which one wall 32 is constituted of a deformable membrane, such as of stainless steel or brass, having a piezoelectric wafer 33 adhering to its outer face. Housing 31 thus defines a pumping chamber 34 which is expansible and contractible by the driving voltages applied to the piezoelectric wafer 33 via the driving lead 35 from the control unit 21 (FIG. 2) of the implanted controller 2. Membrane 33 further includes a sensor 36 which senses the actuations of the piezoelectric wafer 33, particularly the magnitude and frequency of the deformations of membrane 32. Sensor 36, for example, may be a section of the electrode to which the driving lead 35 is connected and electrically insulated from that section. The information sensed by sensor 36 is transmitted via lead 37 to control unit 21 of the implanted controller 2, which, in the light of the known parameters, can translate this information into volume, and thereby, into a measurement of the drive liquid (and feed liquid) pumped.

Pump 3 further includes two valves, namely: valve $V_1$ in conduit 38 (FIG. 1) leading from one end of the pumping chamber 34 to the feed liquid unit 4, and valve $V_2$ in conduit 39 leading from the opposite end of chamber 34 to the liquid drive unit 5. Both valves $V_1$, $V_2$ are solenoid-actuated and are driven by control unit 21 of the implanted controller 2 via leads 40, as shown by the block diagram in FIG. 2.

The insulin-feed unit 4 includes a collapsible bag 41 (FIG. 1) serving as a reservoir for the insulin (or, as mentioned earlier, another feed drug or liquid) to be delivered by the illustrated delivery system. Collapsible reservoir 41 is enclosed within a rigid housing 42. The space or chamber 43 between the inner face of housing 42 and the outer face of the collapsible reservoir 41, constituting a displaceable separator wall between the reservoir and chamber 43, communicates, via conduit 44, valve $V_1$ and conduit 38, with one side of the pumping chamber 34. The interior of the collapsible reservoir 41 communicates, via conduit 45, with the outlet feed tube 7 for feeding thereto the insulin to be delivered to the body.

The drive liquid unit 5 similarly includes a collapsible container 51 enclosed within a rigid housing 52. In this case, however, the space or chamber 53 between the inner face of the housing and the outer face of collapsible container 51 does not communicate with any other device, but rather is sealed and is subjected to a sub-ambient pressure. The interior of collapsible container 51 communicates, via conduit 55, valve $V_2$ and conduit 39, with the respective side of the pumping chamber 34 of pump 3.

The refill fitting 6 communicating with the interior of the insulin reservoir 41 includes a body 61 receiving, at one side, conduit 45 leading to the interior of the insulin reservoir 41, and, at the opposite end, the feed tube 7 through which the insulin is delivered. Body 61 is formed with a bore 62 substantially aligned with the ports for conduit 45 and feed tube 7 and at right angles thereto, which bore leads to a compartment 63 at the lower end of the fitting. The upper end of the fitting includes a rubber plug 64 closing the upper end of bore 62, the plug being retained in place by an apertured retainer ring 65.

Compartment 63 at the lower end of fitting 6 contains an electrical switch, including a membrane 66 carrying one electrical contact 67 which may be brought into engagement with another contract 68 fixed centrally of the inner face of the compartment wall. It will be seen that this electrical switch is normally open, but is automatically closed upon the deformation of membrane 66; this occurs upon the application of the refill unit 8 into the fitting 6, as will be described below. When switch contacts 67, 68 are closed, an electric signal is transmitted via leads 69 to control unit 21 (FIG. 2) of the implanted controller 2.

As indicated earlier, the feed tube 7 from fitting 6 delivers the feed liquid (e.g., insulin) from reservoir 41 to the subject's body upon the actuation of pump 3. Tube 7 includes a one-way valve 71 which permits the insulin to pass in the direction from reservoir 41 to the subject's body, but not in the reverse direction.

Refill unit 8 includes a container 81 for a supply of insulin (or other feed liquid) to be used for refilling reservoir 41. The refill unit 8 further includes a hollow needle or tube 82 depending downwardly from the bottom of container 81. When the insulin reservoir 41 is to be refilled, the hollow needle 82 is inserted into the refill fitting 6, with the needle piercing plug 64 of the fitting so as to establish communication between the interior of refill container 81 and reservoir 41. When the hollow needle 82 is thus inserted, the lower end of the needle engages membrane 66 within compartment 63 of the refill fitting 6, deflecting the membrane to bring its contact 67 into engagement with the fixed contact 68. This transmits an electric signal via leads 69 to control unit 21 of the implanted controller 2.

The liquid delivery system illustrated in the drawings may be used in the following manner:

As noted above, the complete system illustrated in FIGS. 1 and 2 is intended to be implanted into the body of the patient, except for the refill unit 8 and the external controller 10. The refill unit 8 is to be applied whenever it is desired to refill the insulin (or other feed liquid) reservoir 41; and the external controller 10, which may be a hand-held unit normally retained in a holder carried externally of the body, is to be used only when it is desired to input information into the implanted controller 2 or to output information therefrom.

Before implanting, the interior of collapsible container 51, pumping chamber 34, and chamber 43 between rigid housing 42 and the collapsible insulin reservoir 41, are filled with an air-free non-compressible liquid, such as aerated bubble-free water. This complete volume is then sealed off such that a sub-ambient pressure is present within chamber 53 between the collapsible drive-liquid container 51 and its outer rigid housing 52. This sub-ambient pressure is to be present when the collapsible reservoir 41 of the feed liquid unit 4 is filled with a normal supply of the insulin to be delivered, which filling may be done before implanting or after implanting by a refill operation to be described below.

The implanted portion of the system may then be programmed by the external controller 10 to deliver the feed liquid (insulin) to the body from the collapsible reservoir 41 according to pre-fixed times, rates, etc.

During the delivery mode of operation of the system, pulses are applied by the electronic control unit 21 of the implanted controller 2 to the piezoelectric wafer 33 of pump 3, and the valves $V_1$, $V_2$ are controlled so that the non-compressible liquid within container 51 of the drive liquid unit 5 is pumped by pumping chamber 34 into chamber 43 of the feed liquid unit 4. Thus, during the expansion of pumping chamber 34, valve $V_1$ is closed and then valve $V_2$ is opened so that drive liquid is drawn from container 51 into chamber 34; and during the contraction stroke of the chamber, valve $V_2$ is closed and then valve $V_1$ is opened so that the drive liquid within chamber 34 is pumped into chamber 43 of the feed liquid (insulin) unit 4, thereby pumping a corresponding quantity of the insulin from its collapsible container 41 through its outlet conduit 45 to the feed tube 7, and through the valve 71 of the latter to the body of the patient.

During this delivery mode of operation of the system, sensor 36 senses the magnitude and frequency of the displacements of membrane 32 of chamber 34, and transmits this information via lead 37 to the control unit 21 of the implanted controller 2. Since the dimensions and other parameters of chamber 34 are known, the electronic control unit 21 can compute the precise volume change of chamber 34, and thereby the precise volume of insulin delivered from its reservoir 41 to the body via feed tube 7. The value of this volume of delivered insulin is continuously stored within memory 24 of the electronic control unit 21.

The insulin reservoir 41 may be refilled periodically (e.g. monthly or at any other predetermined interval) by inserting the refill unit 8 into the refill fitting 6, whereupon the system operates according to a refill mode. For initiating this mode, hollow needle 82 of refill unit 8 is inserted through the opening of retainer ring 65 to pierce plug 64 of the refill fitting 6, and to limit against the bottom of its chamber 63. This insertion of the hollow needle 82 establishes communication through the needle and tube 45 between the interior of refill container 81 and the implanted insulin reservoir 41; in addition, the lower end of the needle deflects diaphragm 66 to bring its electrical contact 67 into engagement with the fixed contact 68. This closing of the contacts transmits a signal via leads 69 to the electronic control unit 21 of the implanted controller 2 which signal initiates the refill mode of operation.

During this refill mode of operation, piezoelectric wafer 33 is pulsed to expand and contract chamber 34 as in the delivery mode, but the valves $V_1$ and $V_2$ are controlled in a manner opposite to that during the delivery mode to pump the drive liquid from chamber 43 of the insulin feed unit 4 to the interior of the collapsible container 51 of the drive liquid unit 5. That is to say, during the expansion strokes of pumping chamber 34, valve $V_2$ is first closed and valve $V_1$ is then opened to draw drive liquid from chamber 43 of the drive liquid unit 5 into pumping chamber 34; and during the contraction strokes of chamber 34, valve $V_1$ is first closed and valve $V_2$ is then opened to drive the liquid from chamber 34 into the collapsible container 51 of the drive liquid unit 5. This decrease in volume of chamber 43 draws insulin from the refill unit 8 into the implanted insulin reservoir 41.

The quantity of drive liquid pumped from chamber 43 back into the collapsible container 51 of the drive liquid unit 5 during the refill mode of operation (and thereby the quantity of insulin drawn into its reservoir 41) is also closely monitored by the control unit 21 of the implanted controller 2 via sensor 36. When this latter quantity precisely equals the quantity of insulin which had been previously delivered by the system, as stored in memory 24, the refill mode of operation is automatically terminated. This may be signalled to the user by a visual or sound indicator carried by the external controller 10, but will normally be apparent by the termination of operation of the pump 3.

When the implanted insulin reservoir 41 has thus been refilled by precisely the amount which had been previously delivered. The refill unit 8 may be removed from fitting 6, whereupon the opening of switch contacts 67, 68 automatically returns to the system to the delivery mode of operation, to deliver insulin from the implanted reservoir 41 according to the programmed rates, quantities, time periods, etc.

It will be seen that the described system provides a number of advantages which are particularly important when the system is used as an implantable micro-pump for delivering insulin or other drugs from the implanted reservoir 41. Thus, the drug comes into contact only with the collapsible reservoir 41 and its outlet tube 45, and does not come into contact with any valves or other mechanical elements which would apply shear forces to the drug being delivered, and which thereby could deteriorate the proteins or other ingredients of the drug. Moreover, the pumping pressure is distributed gently along the large area outer face of the collapsible reservoir 41, thereby avoiding turbulent flow which could produce shear forces tending to deteriorate the proteins or other ingredients of the delivered drug. Further, the accuracy in the dosage delivered is precisely monitored by sensor 36 and is precisely controlled by the implanted controller 2. Also, by using an air-free noncompressible liquid as the driving liquid sealed within the system, the possibility of air affecting the accuracy of delivery is virtually eliminated.

Another important advantage is that the pump does not require priming, and is therefore immediately available to precisely pump the drug out of the implanted reservoir 41 during the delivery mode of operation, and into the reservoir during the refill mode of operation. A further advantage is that the refill mode of operation is automatically terminated when the implanted reservoir 41 has been refilled with the precise amount of feed liquid which had been previously delivered; this substantially reduces or eliminates the danger of overfilling or overdosage which can exist when the implanted reservoir is refilled by conventional means, such as by the use of a syringe.

A still further advantage is that the illustrated delivery system is substantially fail-safe in case of malfunction of the pump, since the sub-ambient pressure within chamber 53 of the drive unit 5 will, in the event of malfunction (e.g., of valves $V_1$ or $V_2$) tend to apply a negative pressure rather than a positive pressure to the drug within the implanted reservoir 41, thereby avoiding the danger of undesired delivery of the liquid from reservoir 41 to the body during such a malfunction condition.

While the invention has been described with respect to one preferred embodiment, particularly useful as an implantable micro-pump for delivering insulin or other drug to a living body, it will be appreciated that the invention could advantageously be used in many other applications, and that various modifications and variations could be included, such as the use of a pump other

What is claimed is:

1. A liquid delivery system comprising:
a collapsible reservoir for a feed liquid to be delivered;
a first rigid housing enclosing said collapsible reservoir;
a collapsible container for a drive liquid;
a second rigid housing enclosing said collapsible container for the drive liquid;
a refill container;
and pumping means for selectively pumping said drive liquid either from the drive liquid container into said first rigid housing between its inner face and the collapsible reservoir for pumping the feed liquid therefrom, or out of said first rigid housing into the drive liquid container for refilling said collapsible reservoir with feed liquid from said refill container;
the interior of said second rigid housing being maintained under sub-ambient pressure so that in the event of malfunction of the pumping means, said sub-ambient pressure tends to draw the drive liquid into its collapsible container, and thereby provides fail-safe protection against the pumping out of the feed liquid from its reservoir.

2. The system according to claim 1, wherein said refill container is selectively connectible to said feed liquid reservoir for refilling same.

3. The system according to claim 2, further including means, effective upon connection of said refill container to the inlet of the feed liquid reservoir, for automatically actuating said pumping means to pump the drive liquid into its container, and thereby to cause the supply of feed liquid to be drawn into its reservoir from the refill container.

4. The system according to claim 3, wherein said pumping means are electrically energized and are controlled by a control system including an electrical switch actuated upon the connection of said refill container to the inlet of the feed liquid reservoir.

5. The system according to claim 4, wherein all of said recited elements, except for said refill container, are incorporated within a self-contained unit implantable into a living body.

6. The system according to claim 4, wherein said inlet is normally sealed closed, said refill container including an outlet tube adapted to penetrate said seal and at the same time to actuate said electric switch.

7. The system according to claim 4, wherein said control system includes a memory which continuously stores a value representing the quantity of feed liquid delivered by said pumping means, said pumping means being actuated by said electrical switch to cause a quantity of feed liquid to be drawn into its collapsible reservoir from the refill container corresponding to said stored quantity of feed liquid previously delivered by said pumping means, and thereupon to automatically terminate the operation of the pumping means.

8. The system according to claim 1,
wherein said pumping means comprises: a chamber having at least one wall including a membrane deflectable to expand and contract said chamber and thereby to pump the feed liquid; a drive for deflecting said membrane to expand and contract said chamber; and a sensor sensing the deflections of said membrane to provide a measurement of the quantity of feed liquid pumped by said pumping chamber.

9. A liquid delivery system, comprising: a pumping chamber having at least one wall including a membrane deflectable to expand and contract said chamber and thereby to pump a liquid therefrom; a drive for deflecting said membrane to expand and contract said chamber; and a sensor sensing the deflections of said membrane to provide a measurement of the quantity of the liquid pumped by the pumping chamber.

10. The system according to claim 9, wherein said deflectable membrane includes a piezoelectric wafer.

11. The system according to claim 10, wherein said piezoelectric wafer includes a driving electrode for driving the wafer, and a sensing electrode for sensing the magnitude and frequency of the deflections of the wafer.

12. A liquid delivery system comprising a feed liquid reservoir for a feed liquid to be delivered; a refill container for containing a supply of refill feed liquid, which refill container is selectively connectable to the feed liquid reservoir for refilling same; pumping means for selectively pumping the feed liquid either out from its reservoir for delivering same to another location, or into its reservoir from the refill container for refillling same; and a control system for controlling said pumping means; said control system including a memory which continuously stores a value representing the quantity of feed liquid delivered by said pumping means from said feed liquid reservoir; and control means, effective upon the connection of said refill container to the inlet of the feed liquid reservoir, for automatically operating said pumping means to cause a quantity of feed liquid to be drawn into the feed liquid reservoir from the refill container corresponding to the stored quantity of feed liquid previously delivered by said pumping means, and thereupon to automatically terminate the operation of the pumping means.

13. The system according to claim 12, wherein said pumping means are electrically energized, and said control means includes an electrical switch which is automatically actuated upon the connection of said refill container to the inlet of the feed liquid reservoir.

14. The system according to claim 13, wherein the inlet of the feed liquid reservoir is normally sealed closed, said refill container including an outlet tube adapted to penetrate said seal and at the same time to actuate said electric switch.

15. The system according to claim 12,
wherein said feed liquid reservoir is collapsible and is enclosed within a rigid housing, said system further including a container for a drive liquid which is pumped by said pumping means into said rigid housing between its inner face and the outer face of said collapsible reservoir for the feed liquid.

16. The system according to claim 15, wherein said drive liquid container is also collapsible, and is also disposed within a rigid housing; the space in said latter rigid housing being maintained under sub-ambient pressure, such that in the event of malfunction of the pump means, the sub-ambient pressure tends to draw the drive liquid into its collapsible reservoir, and thereby provides fail-safe protection against the pumping out of feed liquid from its collapsible reservoir.

17. The system according to claim 15,
wherein said collapsible reservoir for the feed liquid including its rigid housing, the drive liquid container, and the pumping means including its control system, are all incorporated in a self-contained unit implantable in a living body.

18. The system according to claim 15,
wherein said feed liquid reservoir is in a feed liquid unit which also includes a drive chamber separated from the feed liquid reservoir by a displaceable separator wall; said pumping means including an expansible and contractable pumping chamber; a first valve connecting said drive chamber to one end of said pumping chamber; a second valve connecting the opposite end of said pumping chamber to the drive liquid container; drive means for expanding and contracting said pumping chamber; and means for selectively controlling said first and second valves so as either to cause the pumping chamber to pump the drive liquid from said drive liquid container into said drive chamber of the feed liquid unit and thereby to deliver feed liquid from said feed liquid reservoir, or to pump the drive liquid from said drive chamber of the feed liquid unit to the drive liquid container and thereby to draw refill feed liquid into said feed liquid reservoir.

19. The system according to claim 18, wherein a wall of said expansible and contractible chamber includes a piezoelectric wafer driven under the control of said control means.

20. The system according to claim 18,
wherein said first valve connects said drive liquid container directly to one end of said pumping chamber, and said second valve connects the opposite end of said pumping chamber to said drive chamber of the feed liquid unit.

21. A liquid delivery system, comprising:
a feed liquid unit including a feed liquid reservoir, and a drive chamber separated therefrom by a displaceable separator wall;
a drive liquid unit including a drive liquid reservoir;
an expansible and contractable pumping chamber;
a first valve connecting said drive chamber of the feed liquid unit to one end of said pumping chamber;
a second valve connecting the opposite end of said pumping chamber to the drive liquid reservoir of the drive liquid unit;
drive means for expanding and contracting said pumping chamber;
a refill container connectible to said feed liquid reservoir for refilling it;
and means for selectively controlling said first and second valves so as either to cause the pumping chamber to pump the drive liquid from said drive liquid reservoir into said drive chamber of the feed liquid unit and thereby to deliver feed liquid from said feed liquid reservoir, or to pump the drive liquid from said drive chamber of the feed liquid unit to the drive liquid reservoir and thereby to draw refill feed liquid from said refill container into said feed liquid reservoir;
said feed liquid reservoir being collapsible and being enclosed within a first rigid housing, and said drive liquid reservoir being also collapsible and also enclosed within a second rigid housing;
the interior of said second rigid housing being maintained under sub-ambient pressure such that in the event of malfunction, the sub-ambient pressure in said second rigid housing tends to draw the drive liquid into its collapsible reservoir, and thereby prevents pumping out the feed liquid from its reservoir malfunction.

22. The system according to claim 21, wherein a wall of said pumping chamber includes a piezoelectric wafer driven to expand and contract said chamber.

23. The system according to claim 21, further including means, effective upon connection of the refill container to the feed liquid reservoir, for automatically actuating the drive to expand and contract said pumping chamber with said first and second valves controlled so as to cause feed liquid to be drawn from the refill container into the feed liquid reservoir.

24. The system according to claim 23, wherein said drive is controlled by a control system which includes a memory continuously storing the quantity of feed liquid delivered by the system, said drive being automatically actuated upon the insertion of the refill container to cause a quantity of feed liquid to be drawn into its feed liquid reservoir corresponding to the quantity stored in said memory as previously delivered by the system, and thereupon to be automatically terminated.

25. The system according to claim 21,
wherein all the recited elements of the system, except for the refill container, are incorporated in a self-contained unit implantable in a living body.

* * * * *